United States Patent [19]

Schneider et al.

[11] Patent Number: 4,980,170
[45] Date of Patent: Dec. 25, 1990

[54] PHARMACEUTICAL FORMULATION AS WELL AS A PROCESS FOR ITS PREPARATION

[75] Inventors: Gerhard Schneider, Baldham; Fritz Stanislaus, Munich; Josef M. Hofer, Grafing; Gert-Ulfert Heese; Hans-Joachim Huber, both of Munich, all of Fed. Rep. of Germany

[73] Assignee: Klinge Pharma GmbH, Munich, Fed. Rep. of Germany

[21] Appl. No.: 373,435

[22] Filed: Jun. 30, 1989

[30] Foreign Application Priority Data

Jun. 30, 1988 [DE] Fed. Rep. of Germany ....... 3822095

[51] Int. Cl.$^5$ .......................... A61K 9/58; A61K 9/62
[52] U.S. Cl. .................................... 424/451; 424/456; 424/461; 424/462

[58] Field of Search ................ 424/458, 456, 451, 461

[56] References Cited

U.S. PATENT DOCUMENTS

| | | | |
|---|---|---|---|
| 4,574,080 | 3/1986 | Roswall et al. | 424/458 |
| 4,681,583 | 7/1987 | Urquhart et al. | 424/458 |
| 4,794,001 | 12/1988 | Mehta et al. | 424/458 |

Primary Examiner—Thurman K. Page
Attorney, Agent, or Firm—Sughrue, Mion, Zinn, Macpeak & Seas

[57] ABSTRACT

A new pharmaceutical formulation as well as a process for its preparation are described, in which the active ingredient in one pharmaceutical form is present in retarded release form in one part, and in another part is present in a form resistant to gastric juices.

14 Claims, 1 Drawing Sheet

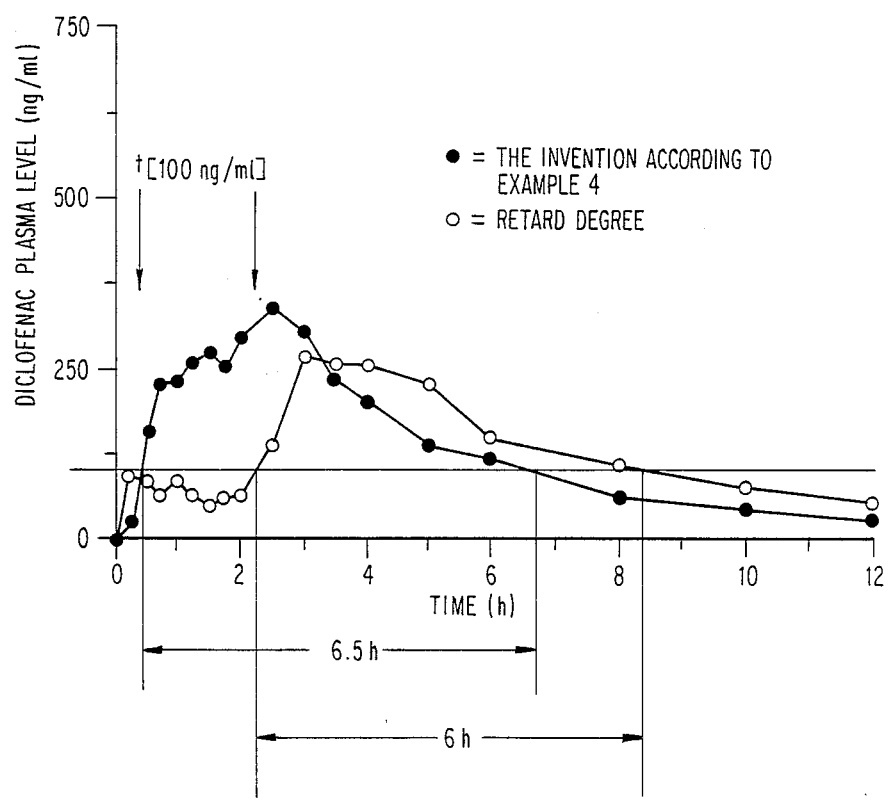

PHARMACEUTICAL FORMULATION AS WELL AS A PROCESS FOR ITS PREPARATION

The invention concerns a new pharmaceutical formulation with controlled release of the active ingredient.

For various applications, pharmaceuticals are desirable which provide for a long-lasting bio-availability. Thus for example in the field of non-steroid antirheumatic agents, with the exception of those from the group of the oxicames, the majority have a plasma elimination half value time of less than approximately 10 hours (H. Fenner "Pharmakokinetik nicht-steroider Antirheumatika", Tempo Medical, volume 12 A/82). These short plasma elimination half value times are desirable to reduce the risk of interactions with other pharmaceuticals, i.e. those which appear more strongly when using non-steroid antirheumatic agents with longer plasma elimination half value times. Here it must be considered that non-steroid antirheumatic agents are more or less strongly subject to a bonding on plasma proteins. The tendency to displace other active ingredients from their bonding with plasma proteins is connected with the strength of this bonding. Thus high bonding affinity is correlated with a high danger of interaction. A clear reduction of the plasma protein bonding as a result of biotransformation or of a deliberate modification of structure has the result of increasing the free (=effective) share of the active ingredient in the plasma, which correspondingly is more rapidly eliminated renally. Thereby a daily multiple application may be necessary.

In all these considerations it must be taken into account that a large number of patients who require long-term treatment with non-steroid antirheumatic agents is of advanced years. In patients of these age groups, the Probability is great that apart from the "antirheumatic" therapy, other medicinal treatments are indicated. The active ingredients which are frequently administered with antirheumatic agents belong, because of their pharmacokinetic properties, to the category of potentially interacting substances and in many cases have a small therapeutic index. Here, for example, active ingredients should be mentioned from the group of the anticoagulants and oral antidiabetic agents, which are also subject to high bonding on plasma proteins.

In order to reduce, for example, the necessary daily multiple application when using non-steroid antirheumatic agents with shorter plasma elimination half value times to a maximally 2 to 3 times administration of the pharmaceutical, the concept of retarded pharmaceutical forms is necessary. Thereby the poor "patient compliance", which unretarded antirheumatic agents have due to the repeated daily administration, is to be countered (lecture by Professor Nürnberg/APV-Course on Antirheumatics, Nürnberg, 19th/20th November 1983). However, due to the relatively short plasma elimination half value times, limits are imposed on the specialist. Thus, for example, Fenner writes in the above mentioned publication in Tempo Medical: "The administration of non-steroid antirheumatic agents in formulations with delayed release of the active ingredient, for example the retard formulations of diclofenac and indometacin, is only suitable under certain circumstances to influence the plasma level course which results from the short plasma elimination half value times of these substances in the desired extent. The retardation leads to a clear flattening of the plasma level curve; however, no control of the plasma level worthy of mention can be effected for longer than about 8 to 10 hours by galenic measures."

On the basis of the illustration of diclofenac plasma level curves after administration of a retard tablet on 100 mg with healthy test persons (n=8) it emerges from the average value curve that in the period between 8 and 10 hours, the diclofenac plasma level sinks to values beneath 100 ng/ml.

The threshold of 100 ng/ml may be regarded as the minimal concentration, exceeding which is necessary to obtain a therapeutic effect.

The specialist is now well aware of the range of problems which is that diclofenac plasma level should be maintained for such length of time that on the one hand the effective duration lasts throughout the night and morning stiffness is prevented, but on the other hand a rapid effect takes place after the consumption of the pharmaceutical.

On this point it follows from the enclosure to a pharmaceutical pack that pain during the night and morning stiffness can be reduced by combined consumption of a tablet resistant to gastric juices with the administration of a suppository or a retard tablet before going to sleep.

However, the combined consumption of a plurality of pharmaceutical forms is always linked with the danger of lack of "patient compliance". Thus in particular in the case of solid pharmaceutical forms the patient may forget to take the second pharmaceutical form or instead of taking a tablet resistant to gastric juices and a retard tablet, he may take two pharmaceutical forms resistant to gastric juices or two retard pharmaceutical forms. The consequence may be the appearance of increased side effects or the omission of rapid reduction in pain.

Therefore it would constitute great progress if it were possible rapidly to reach the necessary plasma level for a therapeutic effect of, for example, approximately 100 ng/ml diclofenac after taking a single pharmaceutical form and to maintain this level for a long period above this minimal concentration.

JP 61/044811 describes a granulate mixture, which is composed of an initial release share and a retarded release share. In the initial release share the active ingredient is already released in the stomach. In the retarded release share, the granulate is wrapped in a membrane which is resistant to gastric juices; in an alternative embodiment, the active ingredient is mixed with the material resistant to gastric juices (thoroughly kneaded).

The combination of an initial release granulate mixture with retarded release active ingredient is also claimed in EP-A-255002.

Non-steroid antirheumatic agents take effect by inhibiting the prostaglandine biosynthesis. Connected therewith is a certain potential for damage/irritation of the stomach mucous membrane by a reduction of those prostaglandines which have a mucous membrane-protective character (Drugs 32 (Suppl. 4): 27 [1986]). On the other hand the majority of non-steroid antirheumatic agents have a direct potential which irritates or damages the mucous membrane. Thus for fenoprofen calcium it could be proven that a pharmaceutical form wrapped to be resistant to gastric juices causes fewer side effects than the uncovered pharmaceutical form (Clin. Pharmacol. Ther., 42: 28 [1987]).

For this reason the route which is described in the two publications named above was not regarded as the more rational way, particularly because from EP-A-255002 it is not discernible whether the plasma levels necessary for the therapeutic effect are achieved quickly after taking the pharmaceutical form, because the first time for withdrawal of blood is only after two hours.

DE-OS 34 31 861 describes a pellet preparation, which contains, inter alia, an active ingredient and a weighting material and is enclosed in a membrane which is resistant to gastric juices. The pellets can be combined in hard gelatine capsules or in the form of tablets with a component, from which the active ingredient is initially released. The blood level curves which are shown were taken from two or four test persons, which is not adequate for the provision of evidence.

The process is based on the desire to extend the duration of the pharmaceutical form in the stomach. Whether this can generally be achieved must be doubted in the light of the literature, from which no influence of the density of the pharmaceutical form, the pellet, emerges for the duration in the stomach (New Eng. J. Med., 304: 1365 [1981]).

For this reason this route to attain the desired effect was not followed, but tests were carried out to discover a different solution. Thus it is the object of the present invention to counter-act a lack of "patient compliance", and to make available a combination preparation which is present in a pharmaceutical form. Furthermore, the object to be achieved is that on taking the combination preparation a reduction in pain should take place as immediately as Possible, i.e. the effect of the pharmaceutical should develop quickly and should remain over the longest possible period. It should be prevented that a substantial part of the active ingredient is already released in the stomach; on the other hand, a part of the active ingredient should very quickly be released in the upper portion of the small intestine, in order to avoid on the one hand damage to the stomach mucous membrane, and on the other hand to achieve a quick alleviation of pain.

The object above is attained in accordance with the invention by a pharmaceutical having controlled release of the active ingredient, wherein the active ingredient is present in a pharmaceutical form partly in retarded release form and partly in a form resistant to gastric juices

BRIEF DESCRIPTION OF THE DRAWINGS

FIG. 1 and 2 represent graphs of the ng/ml verses Time(h).

The designation "resistant to gastric juices", in accordance with the invention, signifies that this component of the pharmaceutical form is stable against gastric juices, whereas in intestinal juices a rapid release of the active ingredient takes place. The definition of a pharmaceutical form resistant to gastric juices, in accordance with the conditions which are described in the supplement to the US Pharmacopia (USP XXI-NF XVI, Supplement No. 5) as well as in the Proposal of the European Pharmaceutical Commission of 17th July 1987 is that the active agent is not released in the acid test (0.1 N HCl, 2h, 37° C.) as to more than 10%, whereas according to USP XXI-NF XVI, Supplement No. 5, with a pH of 6.8 after 45 minutes, the active ingredient must be released as to more than 75%, in order to comply with the requirements of the pharmaceuticals regulations. In accordance with the invention, all possible pharmaceutical forms or parts thereof can be designed to be resistant to gastric juices, including capsules, tablets and dragees, but especially pellets (granulates) and powders. Pellets are particularly preferred according to the invention.

In accordance with the invention, the description "retarded release" is used for the share of the pharmaceutical form which, depending on the selection of the chemical composition and the thickness of the membrane shell, releases the active ingredient in the main in the small intestine in therapeutically required amounts over a longer period (6 to 8 hours). It is desirable that no substantial release of the active ingredient should take place in the gastric juices, because the active ingredient is essentially absorbed in the upper small intestine.

In particular, according to the invention, the active ingredient should be present in or on spherical granulates (pellets) in finely distributed form,.especially in an amorphous, micro-crystalline or molecular-dispersed form, and a part of the pellets should be enclosed by a diffusion membrane which is permeable with retard to the active ingredient and another part of the pellets should be enclosed in a membrane resistant to gastric juices.

It is preferable for the pharmaceutical according to the invention to be enclosed in a capsule, with special preference given to a hard gelatine capsule.

The pharmaceuticals with controlled active ingredient release according to the invention comprise in particular alkaline reacting active ingredients, especially alkaline salts of active ingredients which are present together with adjuvants, preferably active ingredients from the group of the antiphlogistics, analgetics, and antipyretics, with special preference being given to non-steroid antirheumatics.

As the preferred pharmaceutical form, which can meet both requirements, e.g. a capsule suggests itself, preferably a hard gelatine capsule, which contains individual pharmaceutical components, such as for example spherical granulates (pellets). A part of the pellets can be enclosed in a membrane resistant to gastric juices, while another part is surrounded by a diffusion membrane which is permeable with retard for the active ingredient. The share which is enclosed in the membrane resistant to gastric juices ensures a rapid achievement of the therapeutical effect, while that share which is surrounded with the diffusion membrane which is permeable controls the long duration of the effect by the slow release of the active ingredient.

Such a pharmaceutical form having numerous individual components (the co-called "multiple unit" pharmaceutical form) has additional advantages against a single component pharmaceutical form (the so-called "single-unit" form) which in the present case, e.g., could consist of a retard dragee and a dragee resistant to gastric juices, both of which are inserted in hard gelatine capsule: thus in the first case, after dissolution of the hard gelatine capsule in the stomach, which is ended about 5 minutes after taking the pharmaceutical form, several hundred individual pharmaceutical carriers are released, but in the latter case only two. Because they can leave the stomach only within the regular evacuation cycles and because the preferred absorption point for, e.g., non-steroidal antirheumatics is the upper small intestine area, a few large pharmaceutical carriers (diameter>2.0 mm) are more strongly dependent in their absorption and therefore in their effective behaviour on the influence of food taken at the same time (time of food consumption, amount and composition of the food) or on other pharmaceuticals taken at the same time (e.g. tricyclic antidepressive agents, which may slow down the cycle of evacuation of the stomach). See also Wegener, Schaffstein, Börsch in Medizinische Klinik, No. 10, 1988, pages 335–341, and Frömming in Der Internist, No. 27, 1986, pages 32–39.

The expert is also aware that "multiple unit" pharmaceutical forms, in direct comparison with "single unit" pharmaceutical forms, are frequently evacuated substantially quicker from the stomach in the area of the upper small intestine (e.g. Bechgaard, Acta Pharmaceutica Technologica 28, No. 2, 1982, pages 149–157).

The difficulty in the formulation of such a pharmaceutical form for e.g. non-steroid antirheumatic agents is predominantly to be found in the share of the pellets which is enclosed in the membrane resistant to gastric juices. Although the non-steroid antirheumatic agents are different in their chemical structure, they have a number of common properties which determine their dissolution speed/solubility in vitro. Thus the majority of non-steroid antirheumatic agents has an acidic character, whether they are present as heterocyclic enols, or whether they have carboxyl groups. They are connected with pKa values of 4 to 5, above which their basic solubility in the aqueous medium substantially increases. Because of this increase there is frequently an increased interaction with polymers, which are used for the enclosure resistant to gastric juices of pellets. By interaction what is meant is that on the one hand the active ingredient is already released at a pH value of about 5, such as may be present when taking pharmaceuticals simultaneously and when taking food in the stomach, or on the other hand that no complete release of the active ingredient takes place under the pH conditions of the upper small intestine (concerning the possible physiological conditions in the gastro-intestinal tract see the publication by Fricke, MED. MO. PHARM, 11 (5), 1988, pages 169–180).

The early decomposition of pharmaceutical forms resistant to gastric juices in the acidic reacting gastric juice is to be found also in DE-OS 32 33 764.

Based on the fact that oral pharmaceutical forms having a high content of alkaline reacting contents are not certain to be resistant to gastric juices, but already decompose in acidic reacting gastric juice, as a result of which the therapeutic effect of the pharmaceutical is nullified, according to the invention, special measures are taken. Before the application of the coating layer which is resistant to gastric juices on the dosing unit, in accordance with DE-OS 32 33 764, an acid insulating layer is applied, which contains as the main component water-soluble cellulose ether, preferably hydroxypropyl methyl cellulose, as well as additionally 15 to 30% by weight of a water-soluble, solid, crystalline, non-volatile, pharmacologically acceptable mono- and multibase organic acid preferably having a long chain and 5 to 15% by weight of a water-soluble softener, respectively based on the amount of cellulose ether. By this measure it is prevented that by traces of moisture, which either penetrate during the film coating, during incorrect storage or in the acid-aqueous medium of gastric juice into the dosing unit, the alkaline reacting contents ionize the free carboxyl groups of the polymer film forming agent, so that the film forming agent becomes water-soluble. Further penetration of water can then release large amounts of the alkaline contents, so that the entire film coating is dissolved.

The advantage of this process is shown by way of example for the pharmaceutical forms soft gelatine capsules, hard gelatine capsules and film tablets.

For enclosure resistant to gastric -juices, the following pharmacologically acceptable polymers can, for example, be used: copolymers having an anionic character on the basis of methacrylic acid and methacrylic acid methyl ester with different ratios of the free carboxyl groups to the esters and an average molecular weight of 135,000. Typical representatives of these substance classes, e.g. are the acryl resin substances distributed by the firm Röhm-Pharma Eudragit (R)L and Eudragit (R)S or Eudragit (R)L 30 D as aqueous dispersion. A further group comes from the cellulose esters which are esterified with phthalic acid anydride. Trade products of the hydroxypropyl methyl cellulose phthalates (HPMCP) have the designation HB (R)50 or HP (R)55, and are produced, for example, by the firm Shin-Etsu Chemical and Co. HP (R)50 and HP (R)55 differ in their content of methoxy-, hydroxy-propoxy- and carboxybenzol groups (for further information on the polymers which are used see e.g. product informtion from Röhm-Pharma or Shin-Etsu Chemical or the Handbook of Pharmaceutical Excipients, USA 1986).

The pellets which release the active ingredient with retard according to the invention are enclosed in a membrane which is insoluble in the gastric intestinal tract, but is permeable with retard for the active ingredient.

For example the following pharmacologically acceptable polymers may be used for the production of the membranes: acrylic acid ester, methacrylic acid ester, copolymers of the acrylic and methacrylic acid esters, vinylacetates, modified cellulose derivatives etc.

Particularly suitable polymers for the production of the membranes include, inter alia, copolymers of methacrylic acid and of methacrylic acid esters with variable contents of quaternary ammonium groups. which determine the extent of the hydrophility and thereby also the permeability of the polymers.

Typical representatives of this substance class are for example the acryl resins distributed by Röhm-Pharma Eudragit (R)RL and Eudragit (R)RS. These polymers have an ammonium group ratio of about 1:20 (Eudragit (R)RL) and about 1:4=(Eudragit (R)RS)—the molar ratio of the ammonium groups to neutral acrylic acid esters. The permeability of the Eudragit (R)RL/RS membrane can be adjusted at discretion by the mix ratio of the components. The mix ratio necessary for a desired release must be determined for the individual active substances in the manner known per se; normally it is within the limits of 20:80% by weight to 80:20% by weight Eudragit (R)RL Eudragit (R)RS. The permeability of the diffusion membrane can additionally be influenced by the addition of softener substances (phthalic acid dibutyl ester, triacetin etc.) and possibly by further adjuvants, such as talc or magnesium stearate, as separating and smoothing agents.

The following examples and comparative examples are provided for more detailed explanation of the invention.

In comparative example 1, diclofenac-sodium pellets containing the active ingredient were encased in various amounts of HPMCP, without a protective effect resistant to gastric juices at pH 5 coming about.

An equally negative result was obtained after encasing with copolymerisates based on methacrylic acid and methacrylic acid methylester (comparative example 2).

In comparative example 3, a test is shown which was reproduced from the DE-OS 32 33 764 mentioned above. The result is also negative with respect to the stability of the pharmaceutical form at pH 5, possibly because in the present case pellets were encased, and not soft gelatine capsules, hard gelatine capsules or film tablets, which have a substantially smaller surface than pellets.

In comparative examples 4 and 5, with modification of the modus operandi described in DE-OS 32 33 764, no positive result was achieved in the sense of stability of the pharmaceutical form against the influence of simulated gastric juices at pH 5.

On the other hand, placebo pellets which were coated to be resistant to gastric juice based on comparative example 1 were found to be stable at pH 5, in the sense of non-decomposing, so that the assumption can be made that the reason for the instability depends on the alkaline reacting content of the pellets (comparative example 6).

Surprisingly it was then found that a casing resistant to gastric juice at pH 5 can be achieved, when a primer is applied on the pellet containing the active ingredient, consisting of HP (R)55 and—in contrast to DE-OS 32 33 764—a water-insoluble organic acid, and a main coating which consists substantially of HP(R)50. Such encased pellets are stable at pH 5 and completely release the active ingredient within 20 minutes under the simulated conditions of the upper small intestine.

Examples 1 and 2 illustrate the preparation of the inventive pharmaceutical forms, including such pellets encased to be resistant to gastric juices and of the pellets encased in accordance withe the embodiment to be permeable with retard for diclofenac-sodium.

The pharmaceutical forms prepared according to example 2 were tested in a pharmaco-kinetic study with 12 test persons. The test arrangement employed the "cross-over-design".

Earlier pharmaco-kinetic studies, in which inter alia the retard pellets which are also to be used for the inventive combination were investigated, showed for these retard pellets in HGHK a duration until the attainment of medians >100 ng/ml of >2 h from the time of administration.

From the enclosed figure, the effect on which the invention is based becomes clear. On the one hand the pharmaceutical form ensures rapid attainment of plasma levels which are necessary for a therapeutic effect, while on the other hand the time during which the plasma levels exceed the minimal plasma concentration necessary for an effect is comparable with those of a conventional retard pharmaceutical form.

The tradenames which are used in the present specification, especially in the examples and comparative examples, have the following chemical meaning:

Eudragit (R)RL: a polymerisate of acryl and methacryl ester having a small content of quaternary amonium groups for easily permeable retarding film coatings (10 % trimethyl ammonium methacrylate chloride);

Eudragit (R)RS: as above (5% trimethyl ammonium methacrylate chloride), but for retarding film coatings which are hardly permeable;

Eudragit (R)L: anionic polymerisate of methacrylic acid and methacrylic acid methyl ester for film coatings resistant to gastric juices, soluble in intestinal juice as from pH 6;

Eudragit (R)L 30 D: anionic copolymerisate on the basis of methacrylic acid and acrylic acid methyl ester for film coatings resistant to gastric juice, soluble in intestinal juice as from pH 5.5;

Eudragit (R)S: anionic polymerisate of methacrylic acid and methacrylic acid methyl ester for film coatings resistant to gastric juice, soluble in intestinal juice as from pH 7.

The specification of the polymethyl acrylates above corresponds to that which is given in Handbook of Pharmaceutical Excipients of The Pharmaceutical Society of Great Britain on pages 214 to 217.

HP-50: hydroxypropyl methyl cellulose phthalate with an average molecular weight of 20,000 and a methoxy group share of 20 to 25%, a hydroxypropoxy group share of 5 to 10% and a carboxy benzoyl group share of 20 to 24%; viscosity $240 \pm 48$ mNS/m$^2$;

HP-55: hydroxypropyl methyl cellulose phthalate with an average molecular weight of 20,000 and a methoxy group share of 18 to 22%, a hydroxypropoxy group share of 4 to 9% and a carboxy benzoyl group share of 27 to 35%; viscosity $190 \pm 38$ mNs/m$^2$.

HP-50 and HP-55 correspond to the specifications given in the Handbook of Pharmaceutical Excipients of The Pharmaceutical Society of Great Britain on pages 141 to 144.

Comparative Examples and Embodiments According to the Invention

Preparation of the pellets containing the active ingredient:

in accordance with the known pelletizing process, 20 kg of Pellets containing the active ingredient were prepared having the following composition:

| | |
|---|---|
| diclofenac-sodium | 40% |
| saccharose | 55% |
| poly(1-vinyl-2-pyrrolidon) | 4% |
| highly dispersed silicon dioxide | 1% |

Comparative Example 1 for the preparation of encased pellets which are allegedly resistant to gastric juice Respectively 1 kg of the pellets containing the active ingredient were coated in a fluidized bed apparatus with the following coating prescriptions.

| | 1a | 1b | 1c | 1d |
|---|---|---|---|---|
| HP (R)55 | 50 g | 100 g | 150 g | 200 g |
| acetone | 475 g | 950 g | 1,425 g | 1,900 g |
| methanol | 475 g | 950 g | 1,425 g | 1,900 g |

In vitro active ingredient release (%) or organoleptic examination for appearance (the pH value of the release medium was changed after 120 minutes):

| time | pH 1.2 | | | | pH 5.0 | | | |
|---|---|---|---|---|---|---|---|---|
| (min.) | 1a | 1b | 1c | 1d | 1a | 1b | 1c | 1d |
| 30 | | | | | pellets have decomposed | | | |
| 120 | 7.5 | 6.1 | 2.4 | 2.1 | | | | |

Comparative Example 2

1 kg respectively of the pellets containing the active ingredient were coated in a fluidized bed apparatus with the following coating prescriptions:

|  | 2a | 2b | 2c | 2d |
|---|---|---|---|---|
| Eudragit (R)30 D | 167 g | 333 g | 500 g | 667 g |
| talc | 25 g | 50 g | 75 g | 100 g |
| propylene glycol | 5 g | 10 g | 15 g | 20 g |
| water | 117 g | 233 g | 351 g | 468 g |

In vitro active ingredient release (%) or organoleptic examination for appearance:

| time | pH 1.2 | | | | pH 5.0 | | | |
|---|---|---|---|---|---|---|---|---|
| (min.) | 2a | 2b | 2c | 2d | 2a | 2b | 2c | 2d |
| 30 | | | | | pellets have decomposed | | | |
| 120 | 0,7 | 0.7 | 0,5 | 0.2 | | | | |

Comparative Example 3

1 kg respectively of the pellets containing the active ingredient was coated in a fluidized bed apparatus with the following coating prescriptions:

| primer | |
|---|---|
| hydroxypropyl methyl cellulose 15 mPa.s | 30 g |
| hydroxypropyl methyl cellulose 5 mPa.s | 20 g |
| citric acid | 6 g |
| ethanol | 450 g |
| dichloromethane | 450 g |

| main coating | 3a | 3b |
|---|---|---|
| HP (R)50 | 100 g | 200 g |
| 2-propanol | 450 g | 900 g |
| water | 450 g | 900 g |

In vitro active ingredient release (%) or organoleptic examinanion for appearance:

| time | pH 1.2 | | pH 1.5 | |
|---|---|---|---|---|
| (min.) | 3a | 3b | 3a | 3b |
| 30 | | | pellets have decomposed | |
| 120 | 8.0 | 6.1 | | |

Comparative Example 4

1 kg respectively of the pellets containing the active ingredient was coated in a fluidized bed apparatus with the following coating prescriptions:

| primer | |
|---|---|
| HP (R)55 | 50 g |
| citric acid | 7 g |
| acetone | 286 g |
| ethanol | 286 g |

| main coating | 4a | 4b |
|---|---|---|
| HP (R)50 | 100 g | 200 g |
| 2-propanol | 450 g | 900 g |
| water | 450 g | 900 g |

In vitro active ingredient released (%) or organoleptic examination for appearance:

| time | pH 1.2 | | pH 5.0 | |
|---|---|---|---|---|
| (min.) | 4a | 4b | 4a | 4b |
| 30 | | | pellets have decomposed | |
| 120 | 3.2 | 2.1 | | |

Comparative Example 5

1 kg respectively of the pellets containing the active ingredient were coated in a fluidized bed apparatus with the following coating prescriptions:

| primer | |
|---|---|
| hydroxypropyl methyl cellulose 15 mPa.s | 30 g |
| hydroxypropyl methyl cellulose 5 mPa.s | 20 g |
| stearic acid | 143 g |
| ethanol | 450 g |
| dichloromethane | 450 g |

| main coating | 5a | 5b |
|---|---|---|
| HP (R)50 | 100 g | 200 g |
| 2-propanol | 450 g | 900 g |
| water | 450 g | 900 g |

In vitro active ingredient release (%) or organoleptic examination for appearance:

| time | pH 1.2 | | pH 5.0 | |
|---|---|---|---|---|
| (min.) | 5a | 5b | 5a | 5b |
| 30 | | | pellets have decomposed | |
| 120 | 0.2 | 0.5 | | |

Comparative Example 6

In accordance with the known pelletizing process, 2 kg of pellets without active ingredient were prepared with the following composition:

| saccharose | 78% |
|---|---|
| maize starch | 15% |
| poly(1-vinyl-2-pyrrolidon) | 7% |

Respectively 1 kg of the pellets without active ingredient were coated in a fluidized bed apparatus with the following coating prescriptions:

|  | 6a | 6b |
|---|---|---|
| HP (R)50 | 100 g | 200 g |
| acetone | 950 g | 1900 g |
| ethanol | 950 g | 1900 g |

Organoleptic examination for appearance:

| time | pH 1.2 | | pH 5.0 | |
|---|---|---|---|---|
| (min.) | 6a | 6b | 6a | 6b |
| 30 | | | no decomposition of pellets | |
| 120 | no decomposition of pellets | | | |

EXAMPLE 1

Embodiment of the Casing Resistant to Gastric Juices of the Pellets According to the Invention 1 kg respectively of the pellets containing the active ingredient was coated in a fluidized bed apparatus with the following coating prescriptions:

| primer | |
|---|---|
| HP (R)55 | 50 g |
| stearic acid | 143 g |
| talc | 25 g |
| acetone | 286 g |
| ethanol | 286 g |
| main coating | |
| HP (R)50 | 100 g |
| acetylated monoglyceride | 10 g |
| talc | 50 g |
| 2-propanol | 450 g |
| water | 450 g |

In vitro active ingredient release (%) or organoeleptic examination for appearance:

| time (min.) | pH 1.2 | pH 5.0 | pH 6.8 |
|---|---|---|---|
| 5 | | | 5 |
| 10 | | | 74 |
| 20 | | | 103 |
| 30 | | | no decomposition of pellets |
| 120* | 0 | | |

*After 120 minutes, the pH was adjusted from 1.2 to 5.0; after a further 30 minutes, the setting of the pH value was raised to 6.8 (the other conditions corresponded to the European Pharmaceuticals Book).

EXAMPLE 2

Embodiment of the Retard Permeable Casing of the Pellets According to the Invention 1 kg respectively of the pellets containing the active ingredient were coated in a fluidized bed apparatus with the following coating prescription:

| Eudragit (R)RS 100 | 20 g |
|---|---|
| Eudragit (R)RL 100 | 10 g |
| talc | 30 g |
| phthal acid dibutyl ester | 3 g |
| acetone | 215 g |
| 2-propanol | 322 g |

In vitro active ingredient release (%):

| time (h) | pH 1.2 | pH 6.8 |
|---|---|---|
| 1 | <10 | |
| 2 | | 5–30 |
| 4 | | 50–85 |
| 6 | | >70 |

EXAMPLE 3

Embodiment of the Preparation of the Pharmaceutical Forms According to the Invention Respectively 80.5 mg of the pellets encased to be resistent to gastric juices and respectively 130.5 mg of the retarded permeable pellets were dosed into hard gelatine capsules of size 2 using a suitable capsule filling machine. The capsule content had the following composition:

| | gastric juice resistant encased pellets (mg) | retarded permeable pellets (mg) |
|---|---|---|
| diclofenac-sodium | 25.0 | 50.0 |
| saccharose | 34.4 | 68.8 |
| poly/1-vinyl-2-pyrrolidon) | 2.5 | 5.0 |
| highly dispersed silicon dioxide | 0.6 | 1.3 |
| HP (R)55 | 2.5 | |
| HP (R)50 | 5.0 | |
| stearic acid | 7.2 | |
| acetylated monoglyceride | 0.5 | |
| talc | 2.8 | |
| Eudragit (R)RS 100 | | 1.9 |
| Eudragit (R)RL 100 | | 0.7 |
| Talc | | 2.5 |
| phthalic acid dibutyl ester | | 0.3 |
| | 80.5 | 130.5 |

EXAMPLE 4

In another preferred embodiment, 80.5 mg of the pellets encased to be resistant to gastric juice respectively and 195.8 mg respectively of the retard permeable pellets were dosed into hard gelatine capsules of size 1 using a suitable capsule filling machine. The capsule content had the following composition:

| | gastric juice resistant encased pellets (mg) | retarded permeable pellets (mg) |
|---|---|---|
| diclofenac-sodium | 25.0 | 75.0 |
| saccharose | 34.4 | 103.1 |
| poly(1-vinyl-2-pyrrolidon) | 2.5 | 7.5 |
| highly dispersed silicon dioxide | 0.6 | 1.9 |
| HP (R)55 | 2.5 | |
| HP (R)50 | 5.0 | |
| stearic acid | 7.2 | |
| acetylated monoglyceride | 0.5 | |
| talc | 2.8 | |
| Eudragit (R)RS 100 | | 2.9 |
| Eudragit (R)RL 100 | | 1.0 |
| talc | 2.8 | |
| Eudragit (R)RS 100 | | 1.9 |
| Eudragit (R)RL 100 | | 0.7 |
| Talc | | 2.5 |
| phthalic acid dibutyl ester | | 0.3 |
| | 80.5 | 130.5 |

EXAMPLE 5

In another preferred embodiment respectively 80.5 mg of the pellets encased to be resistant to gastric juices and respectively 195.8 mg of the retard permeable pellets were dosed into hard gelatine capsules of size 1 using a suitable capsule filling machine. The capsule content had the following composition:

| | gastric juice resistant encased pellets (mg) | retarded permeable pellets (mg) |
|---|---|---|
| diclofenac-sodium | 25.0 | 75.0 |
| saccharose | 34.4 | 103.1 |
| poly(1-vinyl-2-pyrrolidon) | 2.5 | 7.5 |
| highly dispersed silicon dioxide | 0.6 | 1.9 |
| HP (R)55 | 2.5 | |
| HP (R)50 | 5.0 | |

-continued

|  | gastric juice resistant encased pellets (mg) | retarded permeable pellets (mg) |
|---|---|---|
| stearic acid | 7.2 |  |
| acetylated monoglyceride | 0.5 |  |
| talc | 2.8 |  |
| Eudragit (R)RS 100 |  | 2.9 |
| Eudragit (R)RL 100 |  | 1.0 |
| talc |  | 3.9 |
| phthalic acid dibutyl ester |  | 0.5 |
|  | 80.5 | 195.8 |

We claim:

1. A pharmaceutical composition useful for the controlled release of a non-steroid anti-rheumatic, wherein said composition comprises a capsule containing the following first and second pellets, each of which contains a non-steroid anti-rheumatic:
   (i) first pellets in a form resistant to gastric juices, said first pellets comprising a two-layer membrane resistant to gastric juices comprising a primer coating membrane which has incorporated therein a water-insoluble organic acid and a main coating membrane, and
   (ii) second pellets in retard release form containing a retard permeable diffusion membrane,
wherein the weight ratio of the first pellets resistant to gastric juices to the second pellets in retard release form is form 0.1:1 to 2:1.

2. The pharmaceutical composition as set forth in claim 1, wherein said primer coating membrane and said main coating membrane consist of a cellulose ester derivative, and wherein said retard permeable diffusion membrane comprises one or more acrylic resin layers.

3. The pharmaceutical composition as set forth in claim 1, wherein said capsule is a hard gelatin capsule.

4. The pharmaceutical composition as set forth in claim 1, wherein said non-steroid antirheumatic is a compound selected from the group consisting of acemetacine, diclofenac, fenoprofen, ibuprofen, indometacine, ketoprofen, mefen amino acid, naproxene, sulindac, tiaprofenic acid, tolmetine and a salt of said compounds.

5. The pharmaceutical composition as set forth in claim 1, wherein said non-steroid antirheumatic is disclofenac-sodium.

6. The pharmaceutical composition as set forth in claim 1, wherein said pellets contain from 10 to 95% by weight of said non-steroid antirheumatic.

7. The pharmaceutical composition as set forth in claim 1, wherein said pellets have an average diameter of from 0.4 to 2.0 mm and are encased by a membrane which has a thickness of from 0.001 to 0.5 mm.

8. The pharmaceutical composition as set forth in claim 1, wherein said capsule contains from 10 to 500 mg of said non-steroid antirheumatic.

9. The pharmaceutical composition as set forth in claim 1, wherein the membrane employed in said first pellets resistant to gastric juices is composed of two layers of cellulose ester with different substitution degrees, which are esterified with phthalic acid anhydride.

10. The pharmaceutical composition as set forth in claim 1, wherein the membrane employed in said first pellets resistant to gastric juices is composed of a primer coating membrane which comprises hydroxypropyl methyl cellulose phthalate and a water-insoluble organic acid, and a main coating membrane which comprises hydroxypropyl methyl cellulose phthalate.

11. The pharmaceutical composition as set forth in claim 1, wherein said organic acid is stearic acid.

12. The pharmaceutical composition as set forth in claim 2, wherein said acrylic resin layers of said retard release form are composed of an inner layer difficult to permeate and of an easily permeable outer layer.

13. The pharmaceutical composition as set forth in claim 2, wherein the acrylic resin of said retard release form is a polymerizate of acrylic and methacrylic acid ester containing a small amount of quaternary ammonium groups.

14. The pharmaceutical composition as set forth in claim 1, wherein the two-layer membrane resistant to gastric juices is composed as follows:

Primer coating membrane:

| hydroxypropyl methyl cellulose phthalate | 50 g |
|---|---|
| stearic acid | 143 g |
| talc | 25 g |

Main coating membrane:

| hydroxypropyl methyl cellulose phthalate | 100 g |
|---|---|
| acetylated monoglyceride | 10 g | and wherein the retard permeable diffusion membrane has two layers and is composed of:

| a polymerizate of acrylic acid and methacrylic acid ester containing 5% of trimethyl ammonium methacrylate chloride | 20 g |
|---|---|
| a polymerizate of acrylic acid and methacrylic acid ester containing a small amount of quaternary ammonium groups | 10 g |
| talc | 30 g |
| phthalic acid dibutyl ester | 3 g. |

* * * * *